(12) United States Patent
Chappuis

(10) Patent No.: US 7,338,500 B2
(45) Date of Patent: Mar. 4, 2008

(54) INTERNAL PEDICLE INSULATOR APPARATUS AND METHOD OF USE

(76) Inventor: James L. Chappuis, 3170 Lakeridge Dr., Marietta, GA (US) 30067

( * ) Notice: Subject to any disclaimer, the term of this patent is extended or adjusted under 35 U.S.C. 154(b) by 162 days.

(21) Appl. No.: 11/110,005

(22) Filed: Apr. 20, 2005

(65) Prior Publication Data

US 2005/0240194 A1   Oct. 27, 2005

Related U.S. Application Data

(60) Provisional application No. 60/563,797, filed on Apr. 20, 2004.

(51) Int. Cl.
*A61F 2/00* (2006.01)
(52) U.S. Cl. .................. 606/104; 606/61; 606/96; 606/99; 411/80.5
(58) Field of Classification Search .............. 606/61, 606/86, 96, 99, 103, 104; 623/16.11, 17.11, 623/23.52; 411/80.1, 80.5; 29/278, 280
See application file for complete search history.

(56) References Cited

U.S. PATENT DOCUMENTS

| | | | |
|---|---|---|---|
| 6,093,207 A * | 7/2000 | Pisharodi | 623/17.16 |
| 6,306,156 B1 * | 10/2001 | Clark | 606/216 |
| 6,506,008 B2 * | 1/2003 | Merkli | 412/1 |
| 7,083,621 B2 * | 8/2006 | Shaolian et al. | 606/61 |
| 2004/0267277 A1 * | 12/2004 | Zannis et al. | 606/99 |

* cited by examiner

*Primary Examiner*—Eduardo C. Robert
*Assistant Examiner*—Andrew Yang
(74) *Attorney, Agent, or Firm*—Thomas, Kayden, Horstemeyer & Risley, LLP.

(57) ABSTRACT

An internal pedicle insulator apparatus, comprises an inner insertion rod having a top end and an opposing bottom end; and an outer insertion rod having an upper end and a lower end. The outer insertion rod being arranged and configured to substantially correspond to the inner insertion rod. The inner insertion rod is arranged and configured to slidably engaged inside the outer insertion rod and the inner insertion rod and the outer insertion rod are arranged and configured to position an internal pedicle insulator implant. A method of use is also provided.

13 Claims, 2 Drawing Sheets

(A-A)

(B-B)

INTERNAL PEDICLE INSULATOR APPARATUS AND METHOD OF USE

CROSS-REFERENCE TO RELATED APPLICATION

This application claims priority to copending U.S. provisional application entitled, "Internal Pedicle Insulator Apparatus" having Ser. No. 60/563,797 filed on Apr. 20, 2004, which is entirely incorporated herein by reference.

FIELD OF THE INVENTION

The present invention generally relates to surgical instruments and tools, and in particular, relates to an internal pedicle insulator apparatus.

BACKGROUND OF THE INVENTION

The human spine is composed of a column of thirty-three bones, called vertebra, and their adjoining structures. The twenty-four vertebrae nearest the head are separate bones capable of individual movement and are generally connected by anterior and posterior longitudinal ligaments and by discs of fibrocartilage, called intervetebral discs, positioned between opposing faces of adjacent vertebrae. The twenty-four vertebrae are commonly referenced in three sections. The cervical spine, closest to the head and often referenced as the "neck," comprises the first seven vertebrae of the spine. The thoracic spine and the lumbar spine are below the cervical spine. Each of the vertebra include a vertebral body and a dorsal arch, which enclose an opening, called the vertebral foramen, through which the spinal cord and the spinal nerve pass. The remaining nine vertebrae below the lumbar spine are fused to form the sacrum and the coccyx and are incapable of individual movement.

Degeneration of the lumbar spine can be cause the human spine is composed of a column of thirty-three bones, called vertebra, and their adjoining structures. The twenty-four vertebrae nearest the head are separate bones capable of individual movement and are generally connected by anterior and posterior longitudinal ligaments and by discs of fibrocartilage, called intervetebral discs, positioned between opposing faces of adjacent vertebrae. The twenty-four vertebrae are commonly referenced in three sections. The cervical spine, closest to the head and often referenced as the "neck," comprises the first seven vertebrae of the spine. The thoracic spine and the lumbar spine are below the cervical spine. Each of the vertebra include a vertebral body and a dorsal arch, which enclose an opening, called the vertebral foramen, through which the spinal cord and the spinal nerve pass. The remaining nine vertebrae below the lumbar spine are fused to form the sacrum and the coccyx and are incapable of individual movement.

The degeneration of any portion of the lumbar spine can result in instability of the spine, which can lead to impingement or damage to the spinal cord or nerve roots. Impingement of the spinal column or nerve root can result in pain. Damage to spinal cord or nerve roots can result in reduced motor skills or even paralysis. Degeneration of the lumbar spine can be a result of fractures, tumors or other various degenerative diseases.

It is well known in the art to use pedicle screws for posterior lumbar stabilization procedures. These procedures typically include inserting a pedicle screw posteriorly into the pedicle or pillar of the lumbar spine. The screw is then connected to plates or rods for stabilization of the lumbar spine. A bone graft also can be added to help solidify the stabilization. The pedicle screw may be inserted off center, such as, for example, too medial, which may impinge on the associated nerve root causing pain. This requires a repositioning of the screw. However, even after repositioning there may be an effect on the pedicle wall, which can still cause nerve root irritation. Such procedures are also susceptible to loosening of the screw.

Thus, a heretofore unaddressed need exists in the industry to address the aforementioned deficiencies and inadequacies.

SUMMARY OF THE INVENTION

Preferred embodiments of the present invention provide an internal pedicle insulator apparatus and a method of use. Briefly described, in architecture, one embodiment of the apparatus can be implemented as follows. An internal pedicle insulator apparatus, comprises an inner insertion rod having a top end and an opposing bottom end; and an outer insertion rod having an upper end and a lower end. The outer insertion rod being arranged and configured to substantially correspond to the inner insertion rod. The inner insertion rod is arranged and configured to slidably engaged inside the outer insertion rod and the inner insertion rod and the outer insertion rod are arranged and configured to position an internal pedicle insulator implant.

Preferred embodiments of the present invention can also be viewed as providing methods of use of the internal pedicle insulator apparatus. In this regard, one embodiment of such a method, among others, can be broadly summarized by the following steps: providing an internal pedicle insulator apparatus having an outer insertion rod having an upper end and an opposing lower end; and an inner insertion rod having a top end and a bottom end, the inner insertion rod being axially slidably engaged inside the outer insertion rod; providing an internal pedicle insulator implant; movably engaging the internal pedicle insulator implant with the inner insertion rod; sliding the outer insertion rod along the inner insertion rod toward the internal pedicle insulator implant such that the internal pedicle insulator implant moves along the inner insertion rod.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF THE PREFERRED EMBODIMENTS

Figure 1:
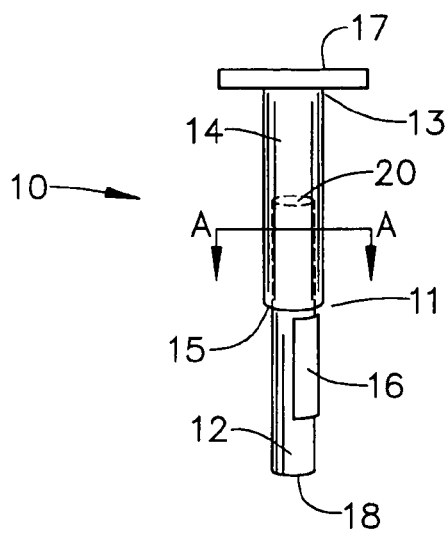
FIG. 1 is a side view of an embodiment of the internal pedicle insulator apparatus of the present invention.

FIG. 1 illustrates one preferred embodiment of an internal pedicle insulator apparatus 10. The internal pedicle insulator apparatus 10 comprises an inner insertion rod 12, an outer insertion rod 14, and an internal pedicle insulator implant 16.

The inner insertion rod 12 has a bottom end 18 and an opposing top end 20. It is preferable that the inner insertion rod 12 has a substantially round cross-section. However, it should be noted that the inner insertion rod 12 can comprise any suitable configuration. The inner insertion rod 12 can comprise any suitable material, such as titanium, as merely one example.

The outer insertion rod 14 has a lower end 11 and an opposing upper end 13. An opening 15 is disposed at the lower end 11. An optional handle 17 can be disposed toward the upper end 13 of the outer insertion rod 14 to facilitate use of the internal pedicle insulator apparatus 10. An opening at the upper end 13 of the outer insertion rod 14 through which the inner insertion rod 12 can pass can also be included (not shown). It is preferable that the outer insertion rod 14 has a substantially round cross-section. It should be noted, however, that the outer insertion rod 14 can comprise any suitable cross-section. The outer insertion rod 14 can comprise titanium, however, it should be understood that the outer insertion rod 14 can comprise any suitable material.

The outer insertion rod 14 is arranged and configured to receive the inner insertion rod 12 through the opening 15 disposed at the lower end 11 of the outer insertion rod 14. The inner insertion rod 12 is preferably slidably inserted into the outer insertion rod 14 such that the upper end 13 of the outer insertion rod 12 substantially corresponds to the top end 20 of the inner insertion rod 12. Similarly, the lower end 11 of the outer insertion rod 14 substantially corresponds with the bottom end 18 of the inner insertion rod 12. The inner insertion rod 12 is laterally slidable within the outer insertion rod 14.

Figure 1A:
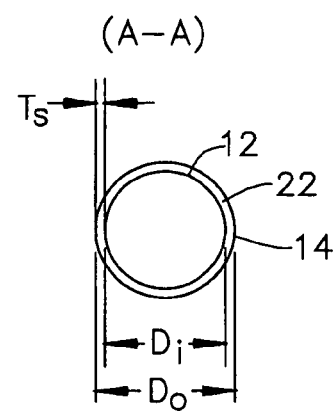
FIG. 1A is a cross-sectional top view of an embodiment of the internal pedicle insulator apparatus illustrated in FIG. 1.

Referring next to FIG. 1A, in one embodiment it is preferable that the outer insertion rod 14 is defined by a diameter $D_o$. The inner insertion rod 12 is defined by a diameter $D_i$. It is preferable that $D_o$ is greater than $D_i$ to facilitate the inner insertion rod 12 being slidably disposed within the outer insertion rod 14. It is further preferable that $D_o$ is less than $D_i$ such as to leave a space 22 having a thickness $T_s$ when the inner insertion rod 16 is disposed within the outer insertion rod 14.

Figure 1B:
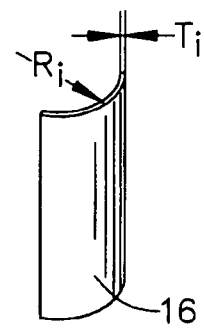
FIG. 1B is a perspective view of an embodiment of an internal pedicle insulator implant of the internal pedicle insulator apparatus illustrated in FIG. 1.

As shown in FIG. 1B, in one embodiment the internal pedicle insulator implant 16 is substantially rectangular in shape and curved. It should be understood, however, that the internal pedicle insulator implant 16 can comprise any suitable shape and configuration. In this embodiment it is preferable that the internal pedicle insulator implant 16 is curved as defined by a radius $R_i$. It is preferable that the radius $R_i$ of the internal pedicle insulator implant 16 substantially corresponds to a pedicle screw 104 with which the internal pedicle insulator implant 16 is to be used. The internal pedicle insulator implant 16 is also defined by a thickness $T_i$. It is preferable that the thickness $T_i$ is greater than the thickness $T_s$ of space 22. The internal pedicle insulator implant 16 preferably comprises Poly Ether Ether-Ketone, but can comprise any suitable material.

Figure 2:
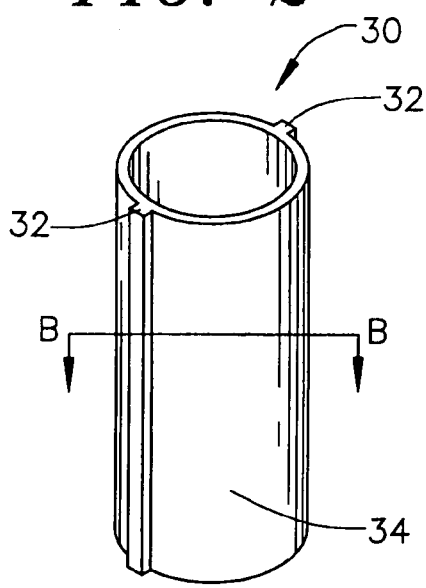
FIG. 2 is a perspective view of an embodiment of an internal pedicle insulator implant of the internal pedicle insulator apparatus illustrated in FIG. 1.
Figure 2A:
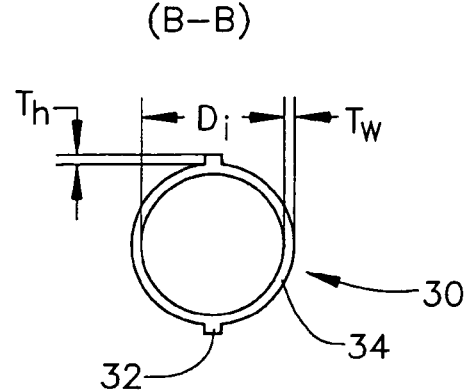
FIG. 2A is a cross-sectional top view of an embodiment of an internal pedicle insulator implant illustrated in FIG. 2.

FIGS. 2 and 2A illustrate another embodiment of an internal pedicle insulator implant 30. The internal pedicle insulator implant 30 is substantially tubular in shape and comprises a wall 34. The internal pedicle insulator implant 30 has a substantially circular cross-section, defined by a diameter $D_i$. The diameter $D_i$ is preferably arranged and configured to substantially correspond to a pedicle screw 104 with which the internal pedicle insulator implant 30 is to be used. Although a substantially circular cross-section is illustrated, it should be understood that the internal pedicle insulator can have any desired cross-sectional shape.

The internal pedicle insulator 30 optionally comprises at least one anti-rotation fin 32 extending outward from the wall 34. The anti-rotation fins 32 can extend the length of the wall 34 of internal pedicle insulator 30 or only a portion of the length. The anti-rotation fins 32 can comprise any configuration that discourage rotation of the internal pedicle insulator 30 when disposed in a desired position. In one embodiment, a thickness $T_w$ of the wall 34 of the internal pedicle insulator implant 30 in addition to a height $T_h$ of an anti-rotation fin 32 extending from the wall 34 is greater than thickness $T_s$ of the space 22 between the inner insertion rod 12 and the outer rotation rod 14 when the inner insertion rod 12 is disposed within the outer rotation rod 14.

In another embodiment the internal pedicle insulator implant 30 includes no anti-rotation fin 32 (not shown). In this embodiment, it is preferable that a thickness $T_w$ of a wall of the internal pedicle insulator implant 30 is greater than the thickness $T_s$ of the space 22 formed by the inner insertion rod 12 and the outer insertion rod 14 when the inner insertion rod 12 is disposed inside the outer insertion rod 14.

Figure 3:
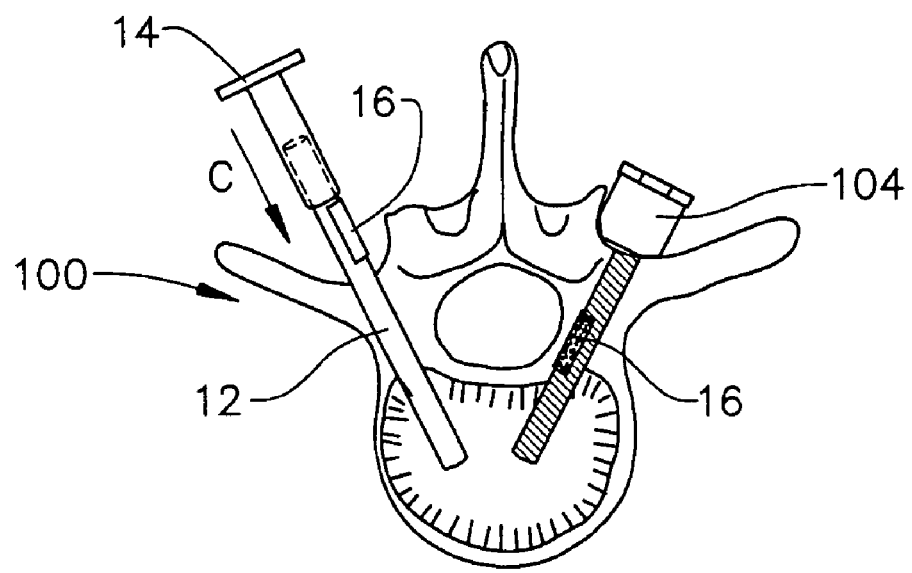
FIG. 3 is a side view of the internal pedicle insulator apparatus illustrated in FIG. 1 in use.

FIG. 3 illustrates the internal pedicle insulator apparatus 10 in use. A pedicle screw with which the internal pedicle insulator implant 16 is to be used is first removed from its position within the vertebral body. The inner insertion rod 12 is positioned as desired in the vertebral body 100, such as in a channel created by the pedicle screw 104. The internal pedicle insulator implant 16 is positioned adjacent the inner insertion rod 12. The outer insertion rod 14 is positioned around the inner insertion rod 12 via the opening 15 disposed at the lower end 11 of the outer insertion rod 14. The outer insertion rod 14 is moved in direction C toward the bottom end 18 of the inner insertion rod 12. As the outer insertion rod 14 is moved in direction C, the outer insertion rod 14 is moved toward the internal pedicle insulator implant 16 until the outer insertion rod 14 engages the internal pedicle insulator 16. Pressure is applied to the outer insertion rod 14 in direction C to slide the internal pedicle insulator 16 along the inner insertion rod 12 toward the vertebral body 100 until the internal pedicle insulator 16 is appropriately positioned within the vertebral body 100. The internal pedicle insulator implant 16 is held in position by friction applied to its curved configuration when properly inserted into position. After the internal pedicle insulator implant 16 is disposed in a desired position, the pedicle screw 104 is returned to its position within the vertebral body.

Figure 4:
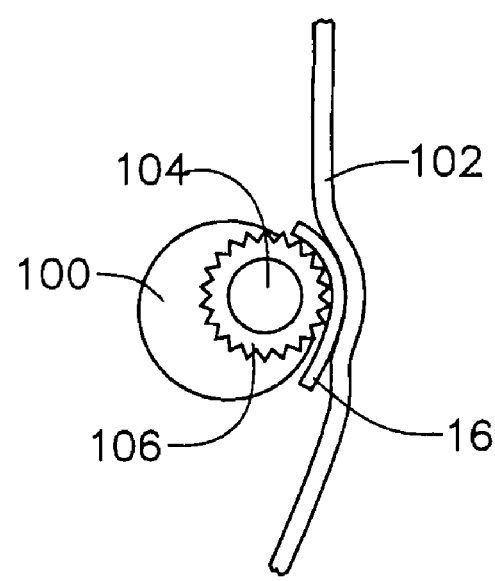
FIG. 4 is a top view of the internal pedicle insulator implant of the internal pedicle insulator apparatus illustrated in FIG. 1 in use.

FIG. 4 illustrates one embodiment of an internal pedicle insulator implant 16 in a desired position. As shown, the internal pedicle insulator implant 16 is positioned between an affected nerve root 102 and a jagged hole 106 in the vertebral body 100 resulting from a compromised pedicle screw 104.

It should be emphasized that the above-described embodiments of the present invention, particularly, a "preferred" embodiment, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein with the scope of this disclosure and the present invention and protected by the following claims.

Therefore, having thus described the invention, at least the following is claimed:

1. A method for using an internal pedicle insulator apparatus, comprising the steps of:
    removing a pedicle screw from an original position within a vertebral body;
    positioning an inner insertion rod in the vertebral body;
    positioning an internal pedicle insulator implant adjacent to the inner insertion rod;
    positioning an outer insertion rod around the inner insertion rod via an opening disposed at a lower end of the outer insertion rod;
    moving the outer insertion rod toward a bottom end of the inner insertion rod toward a internal pedicle insulator implant positioned on the inner insertion rod until the outer insertion rod engages the internal pedicle insulator implant;
    applying pressure to the outer insertion rod to slide the internal pedicle insulator implant along the inner insertion rod toward the vertebral body until the internal pedicle insulator implant is positioned within the vertebral body;
    disposing the internal pedicle insulator implant at a desired position, wherein the internal pedicle insulator implant is held in position by friction applied to its curved configuration when properly inserted into position;
    inserting a pedicle screw into the original position within the vertebral body.

2. The method of claim 1, wherein the internal pedicle insulator implant comprises a substantially rectangular-shaped material having an arcuate surface.

3. The method of claim 1, wherein the internal pedicle insulator implant comprises a substantially tubular-shaped material.

4. The method of claim 1, wherein said inner insertion rod is slidably disposed concentrically within said outer insertion rod.

5. The method of claim 1, wherein said inner insertion rod is substantially tubular in shape and said outer insertion rod is substantially tubular in shape.

6. The method of claim 1, wherein said outer insertion rod has a handle disposed toward an upper end of said outer insertion rod and extending therefrom.

7. The method of claim 1, wherein the internal pedicle insulator implant comprises a substantially rectangular-configured material that is curved.

8. The method of claim 1, wherein the internal pedicle insulator implant comprises a substantially tubular-configured material defined by a wall.

9. The method of claim 8, wherein the internal pedicle insulator implant comprises an anti-rotation fin extending from said wall.

10. The method of claim 1, wherein the step of inserting a pedicle screw further comprises inserting the screw into a position within the vertebral body such that the internal pedicle insulator implant is between a nerve and the inserted pedicle screw.

11. The method of claim 1, wherein said step of disposing the internal pedicle insulator implant at a desired position further includes positioning the internal pedicle insulator implant between a nerve and a hole in the vertebral body.

12. The method of claim 1, wherein said step of positioning an inner insertion rod in the vertebral body further includes positioning said inner insertion rod in a channel created by a pedicle screw.

13. The method of claim 1, wherein the internal pedicle insulator implant assists in retaining a pedicle screw in the vertebral body.

* * * * *